United States Patent [19]

Kinanen et al.

[11] 4,123,702
[45] Oct. 31, 1978

[54] METHOD FOR CLASSIFYING AND MEASURING OF TIMBERS

[76] Inventors: Ilmari Kinanen, Lansiportti 1 E 27, 02210 Espoo 21; Jim Duncker, Anjankuja 2E, 02230 Espoo 23, both of Finland

[21] Appl. No.: 835,575

[22] Filed: Sep. 22, 1977

Related U.S. Application Data

[63] Continuation-in-part of Ser. No. 657,768, Feb. 13, 1976, abandoned.

[51] Int. Cl.² ............................................. G01R 27/04
[52] U.S. Cl. ................................. 324/58.5 A; 209/576
[58] Field of Search ..................... 324/58.5 A, 58.5 B; 209/111.5

[56] References Cited

U.S. PATENT DOCUMENTS

| | | | |
|---|---|---|---|
| 2,659,860 | 11/1953 | Breazeale | 324/58.5 A |
| 3,498,112 | 3/1970 | Howard | 324/58.5 A X |
| 3,501,692 | 3/1970 | Kluck | 324/58.5 A |
| 3,534,260 | 10/1970 | Walker | 324/58.5 A |
| 3,562,642 | 2/1971 | Hochschild | 324/58.5 B |
| 3,786,330 | 1/1974 | Inoue et al. | 324/58.5 B |
| 3,810,005 | 5/1974 | Bennion et al. | 324/58.5 A |

Primary Examiner—Stanley T. Krawczewicz
Attorney, Agent, or Firm—Robert Ames Norton; Saul Leitner

[57] ABSTRACT

Lumber is classified in terms of knots. The method used employs high frequency radio energy and a detector responsive to phase to detect the energy passing through the lumber. The knots exhibit a different dielectric constant, the real part of which is different from normal wood, and the difference in phase of the radiation detected effects the measurement. Preferably, the frequency radiation is near 10 GHz.

1 Claim, 1 Drawing Figure

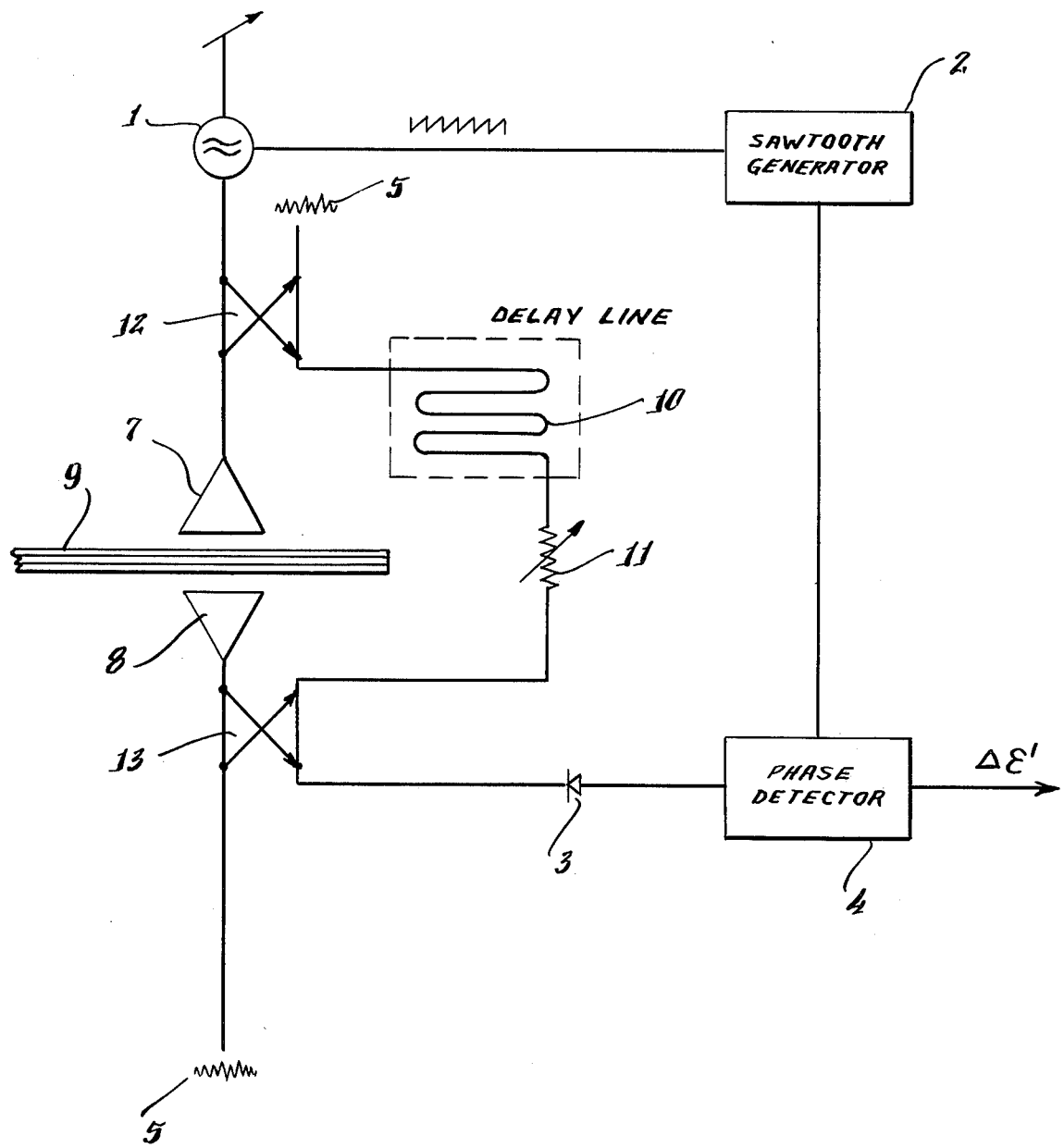

METHOD FOR CLASSIFYING AND MEASURING OF TIMBERS

RELATED APPLICATIONS

This application is a continuation-in-part of our earlier application Serial No. 657,768, filed Feb. 13, 1976, which earlier application is now abandonded.

BACKGROUND OF THE INVENTION

Lumber is sorted and classified primarily on the basis of the number of knots therein. The closest prior art to the present invention is represented by the Bennion and West U.S. Pat. No. 3,810,005, May 7, 1974. In this patent, microwave radiation is passed through the lumber as it is moved past the source of wave, and two detectors receive the microwave radiation passing through the lumber. Signals on each detector are separately amplified and then are joined and amplified in a variable gain differential amplifier. When a knot passes, there is a sudden change in intensity received by the two detectors, and the differential amplifier then gives a signal which is used to trigger a marking device on the lumber. There is a level sensing device which differentiates between gradual changes and the sudden change when a knot passes. Thus different degrees of moisture in the lumber can be cancelled out, and a false knot indication is not given.

SUMMARY OF THE INVENTION

The present invention applies frequency modulated microwave radiation to one side of the lumber, for example a Varactor-synchronized Gunn Oscillator. The phase of the radiation passing through the lumber is shifted by, for example, a wave guide of constant length, for example 20 wavelengths, and is of such length that there is a 180° phase shift. The signals received by the detector are at a minimum when the phase shift is 180°. If a board is free of knots, this minimum does not shift, but when a knot passes through, the minimum point moves and the phase shift is detected. The detection is measured by conventional circuits, including a diode and a comparator circuit synchronized with the saw-tooth generator which produces the frequency of the frequency modulated wave passing through the lumber to be classified. If necessary, the level of the signal is adjusted by a variable attenuator so that it is the same level in each branch.

The phase shift measurement which signals the passage of a knot is very sharp and is unaffected by humidity changes, even sudden humidity changes. Such sudden humidity changes do not affect the phase shift to anything like the same degree as does the passage of a knot. The present invention, therefore, is more reliable and more accurate and is unaffected by changes of environment in the lumber even when these changes, such as humidity, occur quite rapidly.

BRIEF DESCRIPTION OF THE DRAWINGS

A semi-diagrammatic electronic drawing and the lumber passing through is illustrated also diagrammatically.

DESCRIPTION OF THE PREFERRED EMBODIMENTS

In the drawing lumber 9 is passed continuously between two microwave antennas 7 and 8. Antenna 7 is fed by microwave energy which is frequency modulated by a conventional saw-tooth generator 2. A portion of the signal, shown at 5, is coupled by the directional coupler 12 to a delay line 10 of conventional design, and if desired, the amplitude can be adjusted by the variable resistance 11.

Microwave energy passes through the lumber, is received by the antenna 8, which reproduces the frequency modulated signal. A portion of this signal is coupled by the directional coupler 13 to join the portion of the original signal coupled by the coupler 12 and delayed, as has been described. The composite signal then passes through the diode 3 into a comparator 4, which is also of conventional design and which receives the saw-tooth signal from the saw-tooth generator 2. The comparator, which is a phase comparator, produces no signal or rather a minimum signal when the phase is 180° apart, which is a function of frequency.

When there is no knot, the frequency at which the signal is at its minimum is steady, and the comparator does not produce a differential signal. However, when a knot passes, the phase of the signal received by the antenna 8 is suddenly changed and, consequently, also the frequency at which the phases are opposite is changed, and the comparator 4 produces a signal, which is symbolized as $\Delta\epsilon'$. This signal is the knot measuring signal and can be used in any way desired. It can be read out or it can be used to trigger a marking device on the lumber as it passes or for any other purpose. Since the differential signal $\Delta\epsilon'$ is not significantly generated by changes of lumber moisture or other conditions, the response is only to knots, and the reliability of the device is at a maximum. Changes in lumber moisture, whether gradual or sudden, do not affect the operation of the device whereas any sudden changes would cause a false reading in the device of the Bennion patent. It is this greatly increased reliability which is the major advantage of the system of the present invention.

We claim:

1. A method for sorting out and classifying timber in terms of knots characterized in that frequency modulated radio energy in the microwave range is applied from at least one transmitting antenna to one side of the lumber, which is passed in front of the antenna; on the other side of the lumber is a receiving antenna; a portion of the frequency modulated signal applied to the lumber is delayed so that at operating frequency the phase of this reference signal is, opposite to the phase of signal coupled through the receiving antenna, the change of frequency at which the sum of the two detected signals is at minimum is a measure of the phase shift caused by the knot.

* * * * *